United States Patent
Huber

(10) Patent No.: US 8,871,786 B2
(45) Date of Patent: Oct. 28, 2014

(54) AZAINDAZOLE AMIDE COMPOUNDS AS CCR1 RECEPTOR ANTAGONISTS

(75) Inventor: John D. Huber, New Canaan, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 109 days.

(21) Appl. No.: 13/643,325

(22) PCT Filed: Apr. 26, 2011

(86) PCT No.: PCT/US2011/033923
§ 371 (c)(1),
(2), (4) Date: Nov. 8, 2012

(87) PCT Pub. No.: WO2011/137109
PCT Pub. Date: Nov. 3, 2011

(65) Prior Publication Data
US 2013/0203803 A1    Aug. 8, 2013

Related U.S. Application Data

(60) Provisional application No. 61/329,592, filed on Apr. 30, 2010.

(51) Int. Cl.
    *C07D 471/04*    (2006.01)
    *A61K 31/437*    (2006.01)
    *A61P 19/02*    (2006.01)
    *A61P 37/08*    (2006.01)

(52) U.S. Cl.
    CPC .................................... *C07D 471/04* (2013.01)
    USPC ........................................... 514/303; 546/120

(58) Field of Classification Search
    CPC ............................ C07D 471/04; A61K 31/437
    USPC ......................................... 546/120; 514/303
    See application file for complete search history.

(56) References Cited

U.S. PATENT DOCUMENTS

| | | | |
|---|---|---|---|
| 4,999,363 A | 3/1991 | Oshima et al. | |
| 5,118,701 A | 6/1992 | Oshima et al. | |
| 5,242,931 A | 9/1993 | Oshima et al. | |
| 5,302,596 A | 4/1994 | Oshima et al. | |
| 5,534,481 A | 7/1996 | Suzuki et al. | |
| 5,612,360 A | 3/1997 | Boyd et al. | |
| 5,616,537 A | 4/1997 | Yokota et al. | |
| 5,670,452 A | 9/1997 | Suzuki et al. | |
| 5,760,028 A | 6/1998 | Jadhav et al. | |
| 5,763,616 A | 6/1998 | Suzuki et al. | |
| 5,770,544 A | 6/1998 | Yokota et al. | |
| 5,973,156 A | 10/1999 | Chambers et al. | |
| 6,025,374 A | 2/2000 | Castro Pineiro et al. | |
| 6,107,321 A | 8/2000 | Madin | |
| 6,211,219 B1 | 4/2001 | MacLeod et al. | |
| 6,326,382 B1 | 12/2001 | Villalobos et al. | |
| 6,331,640 B1 | 12/2001 | Fotouhi et al. | |
| 6,498,255 B2 | 12/2002 | Villalobos et al. | |
| 6,716,978 B2 | 4/2004 | Marfat | |
| 6,784,182 B2 | 8/2004 | Liebeschuetz et al. | |
| 6,803,384 B2 | 10/2004 | Fotouhi et al. | |
| 6,855,715 B1 | 2/2005 | Liebeschuetz et al. | |
| 6,878,725 B2 | 4/2005 | Liebeschuetz et al. | |
| 6,900,196 B2 | 5/2005 | Liebeschuetz et al. | |
| 6,936,611 B2 | 8/2005 | Liebeschuetz et al. | |
| 7,049,297 B2 | 5/2006 | Zhang et al. | |
| 7,053,078 B2 | 5/2006 | Liebeschuetz et al. | |
| 7,129,264 B2 | 10/2006 | Smallheer et al. | |
| 7,223,782 B2 | 5/2007 | Atkinson et al. | |
| 7,429,609 B2 | 9/2008 | Ohi et al. | |
| 7,879,873 B2 | 2/2011 | Cook et al. | |
| 8,008,327 B2 | 8/2011 | DiSalvo et al. | |
| 8,063,065 B2 | 11/2011 | Cook et al. | |
| 8,263,597 B2 | 9/2012 | Kuzmich et al. | |
| 8,293,917 B2 | 10/2012 | Cook et al. | |
| 8,338,610 B2 | 12/2012 | Kuzmich et al. | |
| 2002/0037860 A1 | 3/2002 | D'Andrea et al. | |

(Continued)

FOREIGN PATENT DOCUMENTS

| EP | 345747 A2 | 12/1989 |
|---|---|---|
| EP | 1201268 A2 | 5/2002 |
| JP | 10001478 A | 1/1998 |
| JP | 2008546794 A | 12/2008 |
| WO | 9217475 A1 | 10/1992 |
| WO | 9401415 A1 | 1/1994 |
| WO | 9500509 | 5/1995 |
| WO | 9617842 A1 | 6/1996 |
| WO | 9711945 A1 | 4/1997 |
| WO | 9719073 A1 | 5/1997 |

(Continued)

OTHER PUBLICATIONS

Alzheimer's Disease. Retrieved online Dec. 15, 2010. http:/www.cnn.com/HEALTH/mentalhealt/alzheimers.

(Continued)

*Primary Examiner* — Bruck Kifle
(74) *Attorney, Agent, or Firm* — Michael P. Morris; Anthony P. Bottino

(57) ABSTRACT

Disclosed are CCR1 inhibitor compounds of the formula (I): which are useful in the treatment of autoimmune and other diseases. Also disclosed a pharmaceutical compositions containing the same, and methods of making and using same.

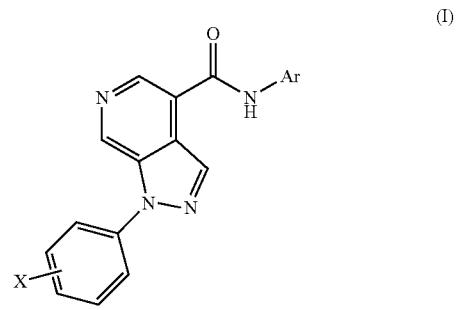

(I)

10 Claims, No Drawings

(56) References Cited

U.S. PATENT DOCUMENTS

| | | | |
|---|---|---|---|
| 2002/0052373 | A1 | 5/2002 | Zorn et al. |
| 2004/0127536 | A1 | 7/2004 | Bhagwat et al. |
| 2005/0009876 | A1 | 1/2005 | Bhagwat et al. |
| 2005/0020564 | A1 | 1/2005 | Atkinson et al. |
| 2005/0108582 | A1 | 5/2005 | Fung |
| 2005/0208582 | A1 | 9/2005 | Ohi et al. |
| 2005/0261339 | A1 | 11/2005 | Ohi et al. |
| 2006/0035938 | A1 | 2/2006 | Bladh et al. |
| 2006/0252781 | A1 | 11/2006 | Basarab et al. |
| 2006/0281739 | A1 | 12/2006 | Gadek et al. |
| 2007/0004761 | A1 | 1/2007 | Basarab et al. |
| 2008/0262040 | A1 | 10/2008 | Callahan et al. |
| 2008/0280956 | A1 | 11/2008 | Gilligan et al. |
| 2009/0054397 | A1 | 2/2009 | Ohi et al. |
| 2010/0093724 | A1 | 4/2010 | Cook et al. |
| 2011/0034512 | A1 | 2/2011 | Disalvo et al. |
| 2011/0086846 | A1 | 4/2011 | Cook et al. |
| 2011/0137042 | A1 | 6/2011 | Razavi et al. |
| 2011/0230521 | A1 | 9/2011 | Cook et al. |
| 2011/0294808 | A1 | 12/2011 | Kuzmich et al. |
| 2012/0035370 | A1 | 2/2012 | Cook et al. |
| 2012/0136158 | A1 | 5/2012 | Cook et al. |
| 2012/0270870 | A1 | 10/2012 | Cook et al. |
| 2012/0270879 | A1 | 10/2012 | Cook et al. |
| 2012/0322790 | A1 | 12/2012 | Betageri et al. |

FOREIGN PATENT DOCUMENTS

| | | | |
|---|---|---|---|
| WO | 9723480 | A1 | 7/1997 |
| WO | 9803504 | A1 | 1/1998 |
| WO | 9923076 | A1 | 5/1999 |
| WO | 0021920 | A1 | 4/2000 |
| WO | 0076970 | A2 | 12/2000 |
| WO | 0076971 | A2 | 12/2000 |
| WO | 0100656 | A2 | 1/2001 |
| WO | 0165218 | A1 | 9/2001 |
| WO | 0210137 | A2 | 2/2002 |
| WO | 03087085 | A1 | 10/2003 |
| WO | 03101968 | A1 | 12/2003 |
| WO | 03105853 | A1 | 12/2003 |
| WO | 2004014905 | A1 | 2/2004 |
| WO | 2004043924 | A1 | 5/2004 |
| WO | 2004056831 | A1 | 7/2004 |
| WO | 2004094372 | A2 | 11/2004 |
| WO | 2005016929 | A1 | 2/2005 |
| WO | 2006091496 | A2 | 8/2006 |
| WO | 2006125119 | A1 | 11/2006 |
| WO | 2007002293 | A2 | 1/2007 |
| WO | 2007028083 | A2 | 3/2007 |
| WO | 2007102883 | A2 | 9/2007 |
| WO | 2008011131 | | 1/2008 |
| WO | 2008089459 | A1 | 7/2008 |
| WO | 2009001129 | A1 | 12/2008 |
| WO | 2009024585 | A2 | 2/2009 |
| WO | 2009037570 | A2 | 3/2009 |
| WO | 2009134666 | A1 | 11/2009 |
| WO | 2009137338 | A1 | 11/2009 |
| WO | 2010036632 | A1 | 4/2010 |
| WO | 2011049917 | A1 | 4/2011 |
| WO | 2011056440 | A1 | 5/2011 |
| WO | 2011071730 | A1 | 6/2011 |
| WO | 2011137109 | A1 | 11/2011 |
| WO | 2012087782 | A1 | 6/2012 |

OTHER PUBLICATIONS

Berge, S. M. et al., "Pharmaceuticals Salts", Journal of Pharmaceutical Sciences, Jan. 1977, vol. 66, No. 1, pp. 1-19.
Caplus: 1990:478384, Bruneau, 1990.
Caplus: 2008:94643, Kitamura, 2008.
Caplus: 2009:583109, Doherty, 2009.
Caplus: 2009:2329372, Loiseleur, 2009.
Carter, P.H. et al., "N—aryl pyrazoles,indazoles and azaindazoles as antagonists of CC chemokine receptor 1: patent cooperation treaty applications WO2010036632, WO2009134666 and WO2009137337". Expert Opinion Ther. Patents, 2010, 20(11), p. 1-10.
Cheng, J-F, et al., "CCR1 Antagonists". Molecular Diversity, Kluwer Academic Publishers, vol. 12, No. 1, Jun. 17, 2008, p. 17-23.
Conlon, K. et al., "Comparison of lymphokine secretion and mRNA expression in the CD45RA+ and CD45RO+ subsets of human peripheral blood CD4+ and CD8+ lympocytes". European Journal of Immunology, 1995, vol. 25, p. 644-648.
Engbersen, J.F.J. et al., "Synthesis of 2-Aminomethyl-1,10-phenanthroline. A new Chelating Agent and Versatile Synthon for other Chelating Compounds", Journal of Heterocyl Cehm., 1986, vol. 23, pp. 989-990.
Finar, I.L. et al. The Beckmann Rearrangement of Some Pyrazolyl Oximes. Journal Chemical Soc. Sec. C, 1969, p. 1495-1499.
Gerard, C. et al., "Chemokines and disease". 2001 Nature Publishing Group, Chemokine Reviews, Nature Immunology, vol. 2, No. 2, Feb. 2001, p. 108-115.
Haringman, J.J. et al., "Chemokine blockade and chronic inflammatory disease: proof of concept in patients with rheumatoid arthritis". Ann Rheum Dis, 2003, 62, p. 715-721.
Karpus, W. J. et al., "An Important Role for the Chemokine Macrophase Inflammatory Protein-1a in the Pathogenesis of the T Cell-Mediated Autoimmune Disease, Experimental Autoimmune Encephalomyelitis". The American Association of Immunologists, 1995, p. 5003-5010.
Koch, A. E., et al., "Macrophase Inflammatory Protein-1a. A Novel Chemotactic Cytokine for Macrophages in Rheumatoid Arthritis". The Journal of Clinical Investigation, Inc., vol. 93, Mar. 1994, p. 921-928.
Koch, A.E. et al., "Epithelial Neutrophil Activating Peptide-78: A Novel Chemotactic Cytokine for Neutrophils in Arthritis". The Journal of Clinical Investigations, Inc. vol. 94, Sep. 1994, p. 1012-1018.
Plater-Zyberk, C. et al., "Effectof a CC chemokine receptor antagonist on collagen induced arthritis in DBA/1 mice". Immunology Letters, 57, 1997, p. 117-120.
Revesz, L. et al., "Novel CCR1 antagonists with oral activity in the mouse collagen induced arthritis". Bioorganice and Medicinal Chemistry Letters, 2005, p. 1-5.
Trebst, C. et al., "CCR1+/CCR5+ Mononuclear Phagocytes Accumulate in the Central Nervous System on Patients with Multiple Sclerosis." American Journal of Pathology, vol. 159, No. 4, Nov. 2001, p. 1701-1710.
Volin, M.V. et al., "RANTES Expression and Contribution to Monocyte Chemotaxix in Arthritis". Clinical Immunology and Immunopathology, vol. 89, No. 1, Oct. 1998, Article II984590, p. 44-53.
International Search Report and Written Opinion for PCT/US2011/033923 mailed Oct. 6, 2011.
Gerard, C. et al., "Chemokines and Disease." Nature Immunology, 2001, vol. 2, pp. 108-115.
Horuk, R. "Chemokine Receptor Antagonists: Overcoming Developmental Hurdle." Nature Reviews Drug Discovery, 2009, vol. 8, pp. 23-33.
Pease, J. et al., "Chemokine Receptor Antagonists: Part 2." Expert Opin. Ther. Patents, 2009, vol. 19, pp. 199-221.
Tak, P. et al., "Chemokine receptor CCR1 antagonist CCX354-C treatment for rheumatoid arthritis: CARAT-2, a randomised, placebo controlled clinical trial." 2012, Ann Rheum Dis., pp. 1-10.

US 8,871,786 B2

AZAINDAZOLE AMIDE COMPOUNDS AS CCR1 RECEPTOR ANTAGONISTS

APPLICATION DATA

This application claims benefit to U.S. provisional application Ser. No. 61/329,592 filed Apr. 30, 2010.

BACKGROUND OF THE INVENTION

1. Technical Field

This invention relates to azaindazoles that are useful as antagonists of CCR1 activity and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

2. Background Information

Chemotactic Cytokine Receptor 1 (CCR1) belongs to a large family (>20) of chemotactic cytokine (chemokine) receptors that interact with specific chemokines (>50) to mediate leukocyte trafficking, granule exocytosis, gene transcription, mitogenic effects and apoptosis. Chemokines are best known for their ability to mediate basal and inflammatory leukocyte trafficking. The binding of at least three chemokines (MIP-1 alpha/CCL3, MCP3/CCL7 and RANTES/CCL5) to CCR1 is responsible for the trafficking of monocytes, macrophages and TH1 cells to inflamed tissues of rheumatoid arthritis (RA) and multiple sclerosis (MS) patients (Trebst et al. (2001) *American J of Pathology* 159 p. 1701). Macrophage inflammatory protein 1 alpha (MIP-1 alpha), macrophage chemoattractant protein 3 (MCP-3) and regulated on activation, normal T-cell expressed and secreted (RANTES) are all found in the CNS of MS patients, while MIP-1 alpha and RANTES are found in the CNS in the experimental autoimmune encephalomyelitis (EAE) model of MS (Review: Gerard and Rollins (2001) *Nature Immunology*). Macrophages and Th1 cells in the inflamed synovia of RA patients are also major producers of MIP-1 alpha and RANTES, which continuously recruit leukocytes to the synovial tissues of RA patients to propagate chronic inflammation (Volin et al. (1998) *Clin. Immunol. Immunopathology*; Koch et al. (1994) *J. Clin. Investigation*; Conlon et al. (1995) *Eur. J. Immunology*). Antagonizing the interactions between CCR1 and its chemokine ligands is hypothesized to block chemotaxis of monocytes, macrophages and Th1 cells to inflamed tissues and thereby ameliorate the chronic inflammation associated with autoimmune diseases such as RA and MS.

Evidence for the role of CCR1 in the development and progression of chronic inflammation associated with experimental autoimmune encephalitis (EAE), a model of multiple sclerosis, is based on both genetic deletion and small molecule antagonists of CCR1. CCR1 deficient mice were shown to exhibit reduced susceptibility (55% vs. 100%) and reduced severity (1.2 vs. 2.5) of active EAE (Rottman et al. (2000) *Eur. J. Immunology*). Furthermore, administration of small molecule antagonist of CCR1, with moderate affinity ($K_i$=120 nM) for rat CCR1, was shown to delay the onset and reduce the severity of EAE when administered intravenously (Liang et al. (2000) *J. Biol. Chemistry*). Treatment of mice with antibodies specific for the CCR1 ligand MIP-1 alpha have also been shown to be effective in preventing development of acute and relapsing EAE by reducing the numbers of T cells and macrophages recruited to the CNS (Karpus et al. (1995) *J. Immunology*; Karpus and Kennedy (1997) *J. Leukocyte Biology*). Thus, at least one CCR1 ligand has been demonstrated to recruit leukocytes to the CNS and propagate chronic inflammation in EAE, providing further in vivo validation for the role of CCR1 in EAE and MS.

In vivo validation of CCR1 in the development and propagation of chronic inflammation associated with RA is also significant. For example, administration of a CCR1 antagonist in the collagen induced arthritis model (CIA) in DBA/1 mice has been shown to be effective in reducing synovial inflammation and joint destruction (Plater-Zyberk et al. (1997) *Immunology Letters*). Another publication described potent antagonists of murine CCR1 that reduced severity (58%) in LPS-accelerated collagen-induced arthritis (CIA), when administered orally (*Biorganic and Medicinal Chemistry Letters* 15, 2005, 5160-5164). Published results from a Phase Ib clinical trial with an oral CCR1 antagonist demonstrated a trend toward clinical improvement in the absence of adverse side effects (Haringman et al. (2003) *Ann. Rheum. Dis.*). One third of the patients achieved a 20% improvement in rheumatoid arthritis signs and symptoms (ACR20) on day 18 and CCR1 positive cells were reduced by 70% in the synovia of the treated patients, with significant reduction in specific cell types including 50% reduction in $CD4^+$ T cells, 50% reduction in $CD8^+$ T cells and 34% reduction in macrophages.

Studies such as those cited above support a role for CCR1 in MS and RA and provide a therapeutic rationale for the development of CCR1 antagonists.

WO 2009/134666, WO 2009/137338 and US 2008-0261975 A1 each describe small molecule compounds which are CCR1 receptor antagonists, the contents of which are incorporated herein by reference in their entirety.

BRIEF SUMMARY OF THE INVENTION

The present invention provides novel compounds which block the interaction of CCR1 and its ligands and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In the broadest generic embodiment, there is provided a compound of the formula (I):

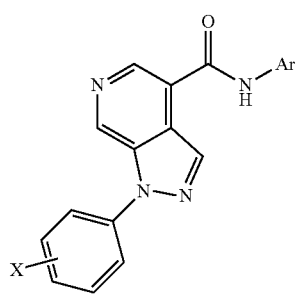

(I)

wherein
Ar is phenyl, naphthyl, 5- or 6-membered monocyclic heteroaryl ring or a bicyclic heteroaryl ring each bearing from 0-4 substituents chosen from halogen, $C_{1-5}$ alkyl, $C_{3-7}$ cycloalkyl, $C_{1-5}$ haloalkyl, cyano, nitro, —SR, —OR, —$SO_2R$, —$SO_2NRR^1$, —$NR^1$—$SO_2R$, —$CO_2$—R, —$NRR^1$, —$NR^2C(O)$—R, —$C(O)NRR^1$, aryl ring and 5- or 6-membered heteroaryl ring each ring optionally substituted with 1 or 2 substituents chosen from halogen and $C_{1-5}$ alkyl;
R, $R^1$, and, $R^2$ are each independently hydrogen or $C_{1-5}$ alkyl, and wherein R and $R^1$ can be taken together to form a heterocycle where possible;
X is halogen;
or a pharmaceutically acceptable salt thereof.

In another embodiment of the invention there is provided a compound of the formula (I) according to the embodiments immediately above and wherein
Ar is phenyl, naphthyl, or heteroaryl chosen from aziridinyl, thienyl, furanyl, thiazolyl, isothiazolyl, isoxazolyl, oxazolyl, oxadiazolyl, pyrazolyl, thiadiazolyl, tetrazolyl, pyrrolyl, imidazolyl, pyrimidinyl, pyridinyl, pyrazinyl, pyridazinyl, pyranyl, benzofuranyl, indolyl, quinoxalinyl, benzimidazolyl, benzoxazolyl, benzothiazolyl, benzothienyl, quinolinyl, quinazolinyl, naphthyridinyl, indazolyl, triazolyl and purinyl each bearing from 0-3 substituents chosen from halogen, $C_{1-4}$ alkyl, $C_{3-7}$ cycloalkyl, $C_{1-4}$ haloalkyl, nitro, —SR, —OR, cyano, —$SO_2R$, —$SO_2NRR^1$, —$CO_2$—R, —$NRR^1$, —$NR^2C(O)$—R, —$C(O)NRR^1$, phenyl and heteroaryl as defined herein above in this paragraph, each ring optionally substituted with 1 or 2 substituents chosen from halogen and $C_{1-4}$ alkyl;
R, $R^1$, and, $R^2$ are each independently hydrogen or $C_{1-4}$ alkyl;
X is fluorine;
or a pharmaceutically acceptable salt thereof.

In another embodiment of the invention there is provided a compound of the formula (I) according to any of the embodiments above and wherein
Ar is phenyl, pyrazolyl, isoxazolyl, pyridinyl, indolyl, each bearing from 0-3 substituents chosen from halogen, $C_{1-4}$ alkyl, $C_{3-7}$ cycloalkyl, $C_{1-4}$ haloalkyl, nitro, —SR, —OR, cyano, —$SO_2R$, —$SO_2NRR^1$, —$CO_2$—R, —$NRR^1$, —$NR^2C(O)$—R, —$C(O)NRR^1$, phenyl and pyrazolyl, oxadiazolyl, each ring optionally substituted with 1 or 2 substituents chosen from halogen and $C_{1-4}$ alkyl;
X is fluorine and is attached in the -para position on the phenyl ring.

In another embodiment of the invention there is provided a compound of the formula (I) according to any of the embodiments above and wherein
Ar is phenyl, pyrazolyl, isoxazolyl, pyridinyl, indolyl, each bearing from 0-3 substituents chosen from halogen, $C_{1-2}$ alkyl, —$CF_3$, —$SO_2CH_3$, —$SO_2NRR^1$, —$CO_2$—R, —$NR^2C(O)$—R, —$C(O)NRR^1$, phenyl and pyrazolyl, oxadiazolyl, each ring optionally substituted with 1 or 2 substituents chosen from halogen and $C_{1-2}$ alkyl;
R, $R^1$, and, $R^2$ are each independently hydrogen or $C_{1-2}$ alkyl;
or a pharmaceutically acceptable salt thereof.

In another embodiment of the invention there is provided a compound of the formula (I) according to any of the embodiments above and wherein
Ar is chosen from

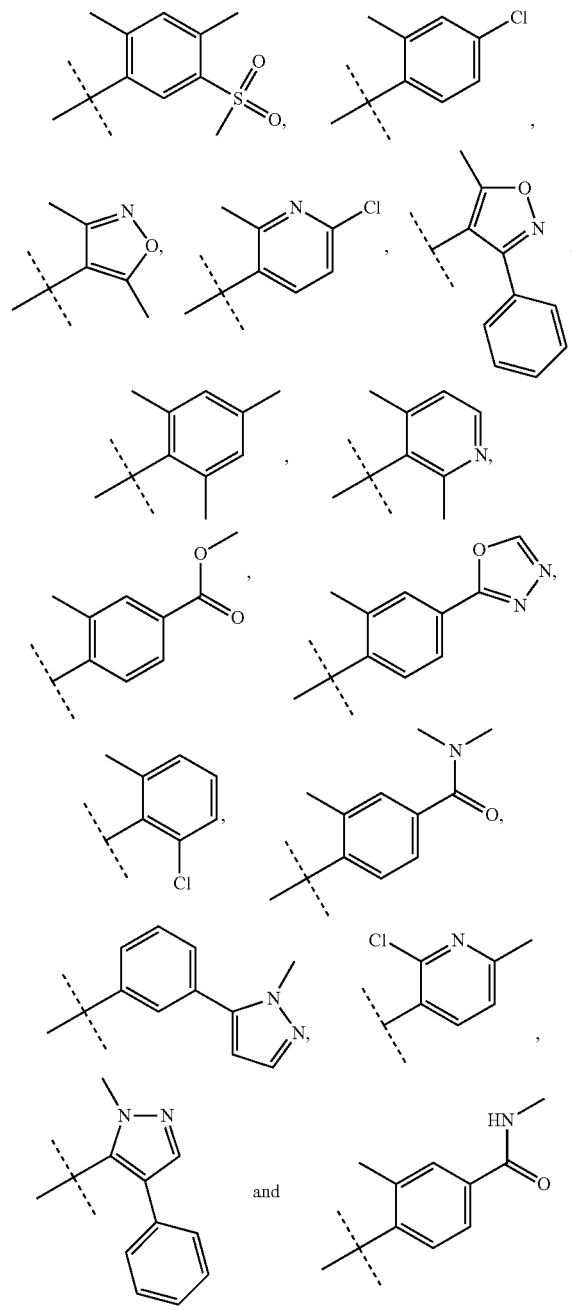

or a pharmaceutically acceptable salt thereof.

In another embodiment, the invention provides compounds in Table I which can be made in view of the general schemes, examples and methods known in the art.

TABLE I

| Compound Number | Structure | Observed [M + H]+ | Retention Time (min.) |
|---|---|---|---|
| 1 | (structure) | 382.1 | 0.9 |
| 2 | (structure) | 362.2 | 0.56 |
| 3 | (structure) | 439.1 | 0.88 |
| 4 | (structure) | 382.2 | 0.92 |

TABLE I-continued

| Compound Number | Structure | Observed [M + H]+ | Retention Time (min.) |
|---|---|---|---|
| 5 | 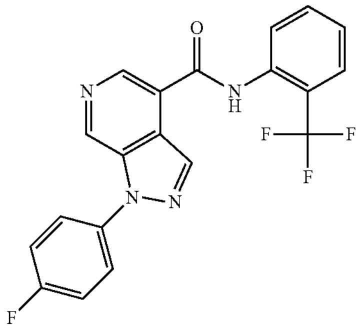 [SMILES: O=C(Nc1ccccc1C(F)(F)F)c1cncc2c1cnn2-c1ccc(F)cc1] | 402.0 | 1.0 |
| 6 | 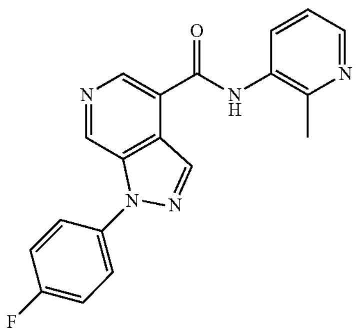 [SMILES: Cc1ncccc1NC(=O)c1cncc2c1cnn2-c1ccc(F)cc1] | 348.2 | 0.58 |
| 7 | 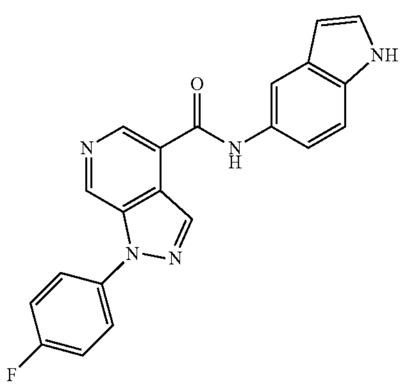 [SMILES: O=C(Nc1ccc2[nH]ccc2c1)c1cncc2c1cnn2-c1ccc(F)cc1] | 372.1 | 0.87 |
| 8 | 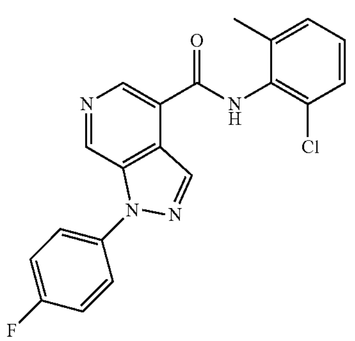 [SMILES: Cc1cccc(Cl)c1NC(=O)c1cncc2c1cnn2-c1ccc(F)cc1] | 381.3 | 0.97 |

TABLE I-continued

| Compound Number | Structure | Observed [M + H]+ | Retention Time (min.) |
|---|---|---|---|
| 9 | 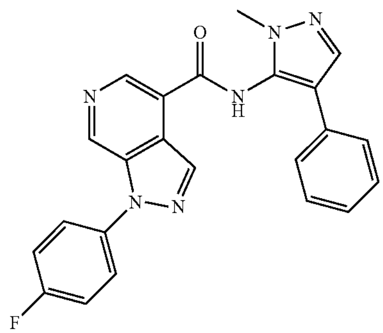 [SMILES: Cn1ncc(-c2ccccc2)c1NC(=O)c1cncc2c1cnn2-c1ccc(F)cc1] | 413.6 | 0.88 |
| 10 | 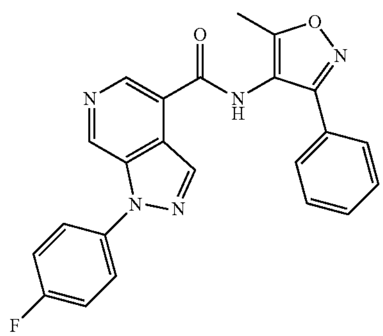 [SMILES: Cc1onc(-c2ccccc2)c1NC(=O)c1cncc2c1cnn2-c1ccc(F)cc1] | 415.0 | 0.95 |
| 11 | 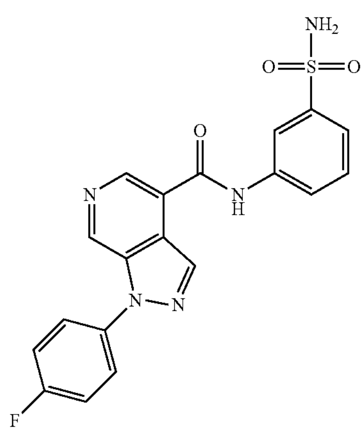 [SMILES: NS(=O)(=O)c1cccc(NC(=O)c2cncc3c2cnn3-c2ccc(F)cc2)c1] | 412.1 | 0.77 |
| 12 | 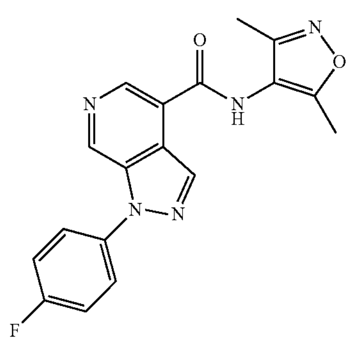 [SMILES: Cc1noc(C)c1NC(=O)c1cncc2c1cnn2-c1ccc(F)cc1] | 352.0 | 0.81 |

TABLE I-continued

| Compound Number | Structure | Observed [M + H]+ | Retention Time (min.) |
|---|---|---|---|
| 13 | 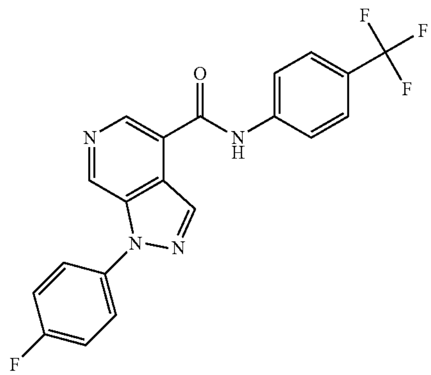 [SMILES: O=C(Nc1ccc(C(F)(F)F)cc1)c1cncc2c1cnn2-c1ccc(F)cc1] | 401.5 | 1.11 |
| 14 | 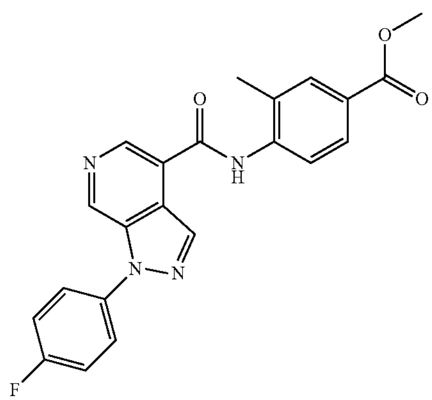 [SMILES: COC(=O)c1ccc(NC(=O)c2cncc3c2cnn3-c2ccc(F)cc2)c(C)c1] | 405.9 | 0.97 |
| 15 | 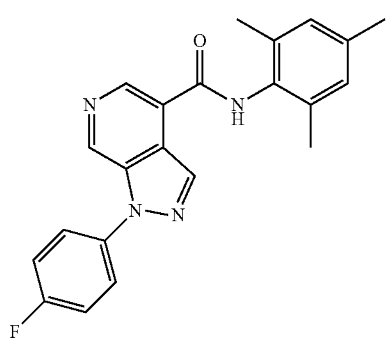 [SMILES: Cc1cc(C)c(NC(=O)c2cncc3c2cnn3-c2ccc(F)cc2)c(C)c1] | 375.1 | 1.02 |
| 16 | 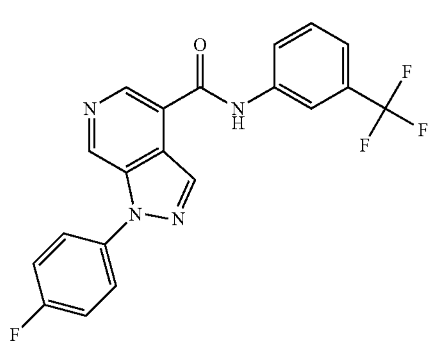 [SMILES: O=C(Nc1cccc(C(F)(F)F)c1)c1cncc2c1cnn2-c1ccc(F)cc1] | 401.2 | 1.12 |

TABLE I-continued

| Compound Number | Structure | Observed [M + H]+ | Retention Time (min.) |
| --- | --- | --- | --- |
| 17 | 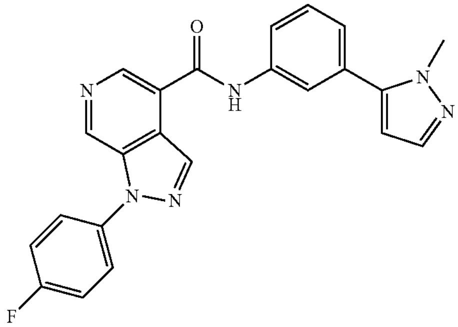 [SMILES: Cn1nccc1-c1cccc(NC(=O)c2cncc3c2cnn3-c2ccc(F)cc2)c1] | 413.2 | 0.93 |
| 18 | 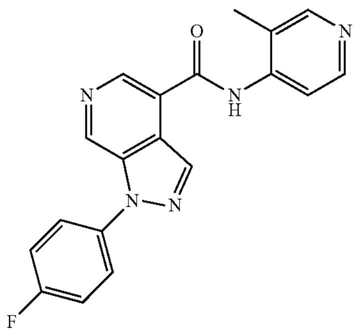 [SMILES: Cc1cnccc1NC(=O)c1cncc2c1cnn2-c1ccc(F)cc1] | 348.2 | 0.58 |
| 19 | 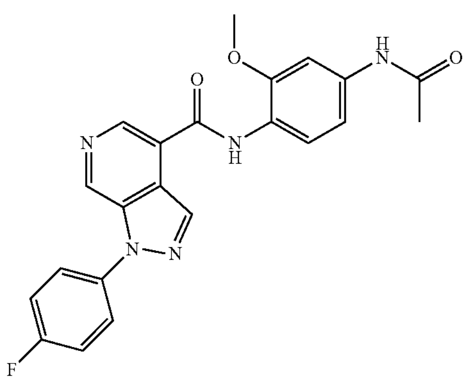 [SMILES: COc1cc(NC(C)=O)ccc1NC(=O)c1cncc2c1cnn2-c1ccc(F)cc1] | 419.4 | 0.86 |
| 20 | 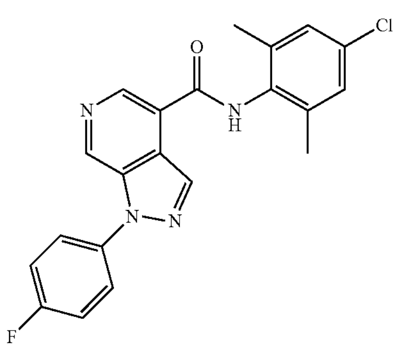 [SMILES: Cc1cc(Cl)cc(C)c1NC(=O)c1cncc2c1cnn2-c1ccc(F)cc1] | 394.8 | 1.1 |

TABLE I-continued

| Compound Number | Structure | Observed [M + H]+ | Retention Time (min.) |
| --- | --- | --- | --- |
| 21 | 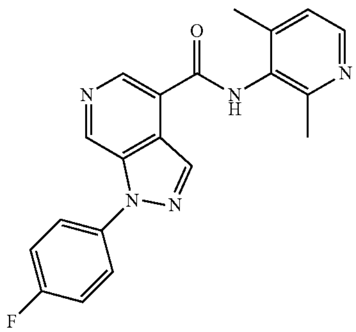 [SMILES: Cc1ccnc(C)c1NC(=O)c1cncc2c1cnn2-c1ccc(F)cc1] | 361.3 | 0.62 |
| 22 | 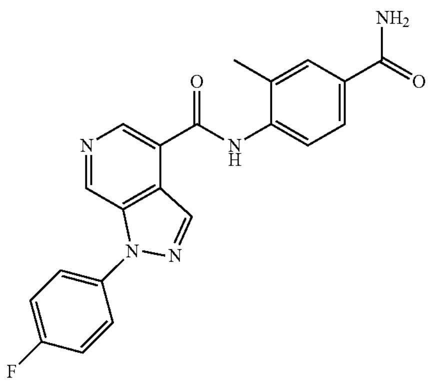 [SMILES: Cc1cc(C(N)=O)ccc1NC(=O)c1cncc2c1cnn2-c1ccc(F)cc1] | 389.4 | 0.78 |
| 23 | 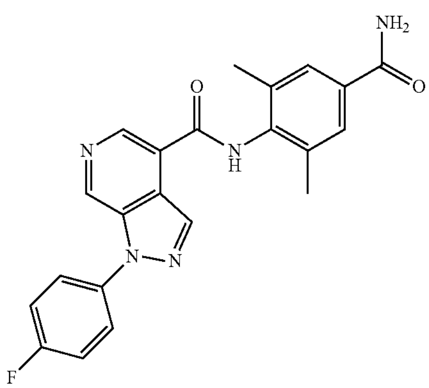 [SMILES: Cc1cc(C(N)=O)cc(C)c1NC(=O)c1cncc2c1cnn2-c1ccc(F)cc1] | 403.4 | 0.79 |
| 24 | 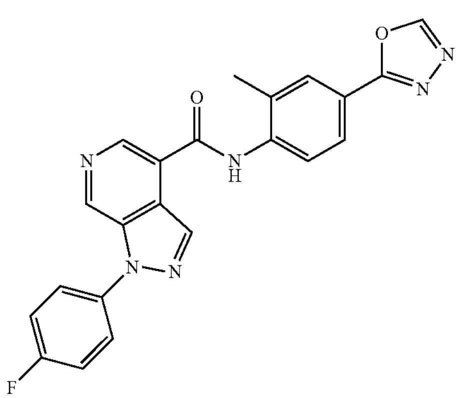 [SMILES: Cc1cc(-c2nnco2)ccc1NC(=O)c1cncc2c1cnn2-c1ccc(F)cc1] | 414.4 | 0.9 |

TABLE I-continued

| Compound Number | Structure | Observed [M + H]+ | Retention Time (min.) |
|---|---|---|---|
| 25 | 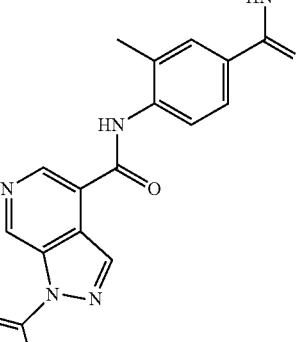 | 403.4 | 0.82 |
| 26 | 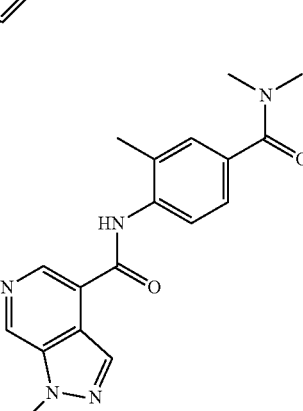 | 417.4 | 0.86 | or the pharmaceutically acceptable salts thereof.

In another aspect the invention relates to compounds—or the pharmaceutically acceptable salts—of the formula (I) as medicaments.

In another aspect the invention relates to pharmaceutical preparations, containing as active ingredient one or more compounds of the formula (I) or the pharmacologically acceptable salts thereof, optionally in combination with conventional excipients and/or carriers.

In another aspect the invention relates to the use of compounds of the formula (I) for preparing a pharmaceutical composition for the treatment of autoimmune diseases.

In another aspect the invention relates to a method of treating autoimmune diseases by administering a therapeutically effective amount of a compound of the formula (I).

In another aspect the invention relates to a pharmaceutical preparation comprising a compound of the formula (I), while the formula (I) compounds are optionally also in the form of the tautomers, the racemates, the enantiomers, the diastereomers, the mixtures thereof, or as pharmaceutically acceptable salts of all the above-mentioned forms.

In another aspect the invention relates to compounds of the invention which also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In another aspect the invention relates to the compounds of the formula (I) which may be used in combination with other active substances which are used in the treatments of autoimmune diseases such as multiple sclerosis, rheumatoid arthritis, psoriasis, atherosclerosis, and chronic obstructive pulmonary disease. Such combinations can be administered either separately or in combination in a pharmaceutical composition.

DEFINITIONS

All terms as used herein in this specification, unless otherwise stated, shall be understood in their ordinary meaning as known in the art. Other more specific definitions are as follows:

Unless specifically indicated, throughout the specification, a given chemical formula or to name shall encompass tautomers and all stereo, optical and geometrical isomers (e.g. enantiomers, diastereomers, E/Z isomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Alkoxy shall be understood to be a $C_{1-n}$-alkyl with an oxygen atom wherein the point of attachment is via the oxygen, for example methoxy: H$_3$CO—.

The term "$C_{3-n}$-cycloalkyl", wherein n is an integer 4 to n, either alone or in combination with another radical denotes a cyclic, saturated hydrocarbon radical with 3 to n C atoms. For example the term $C_{3-7}$-cycloalkyl includes cyclopropyl, cyclobutyl, cyclopentyl, cyclohexyl and cycloheptyl. The structures of the above will be apparent to one skilled in the art.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. The term "aryl" is intended to include all the possible hydrogenated forms. The structures of the above will be apparent to one skilled in the art.

The term "heterocyclyl" means a saturated or unsaturated mono- or polycyclic-ring systems including aromatic ring system containing one or more heteroatoms selected from N, O or S(O)$_r$ with r=0, 1 or 2 wherein none of the heteroatoms is part of the aromatic ring. The term "heterocycle" is intended to include all the possible isomeric forms. Unless otherwise stated, heterocycles include but are not limited to, for example morpholinyl, oxiranyl, tetrahydropyranyl, tetrahydrofuranyl, tetrahydrothiopyranyl, azepanyl, diazepanyl, azetidinyl, pyrrolidinyl, pyrrolinyl, thiomorpholinyl, piperidinyl, dioxalanyl, piperazinyl, 1,3-dioxolanone, 1,3-dioxanone, 1,4-dioxanyl, piperidinonyl, tetrahydropyrimidonyl. The structures of the above will be apparent to one skilled in the art.

The term "heteroaryl" means a mono- or polycyclic-ring systems containing one or more heteroatoms selected from N, O or S(O)r with r=0, 1 or 2 wherein the heteroatom(s) is part of aromatic ring. The term "heteroaryl" is intended to include all the possible isomeric and hydrogenated forms. Unless otherwise stated, such heteroaryls include but are not limited to, for example: aziridinyl, thienyl, furanyl, thiazolyl, isothiazolyl, oxazolyl, thiadiazolyl, tetrazolyl, pyrrolyl, imidazolyl, pyrimidinyl, pyrazinyl, pyridazinyl, pyranyl, benzofuranyl, quinoxalinyl, benzimidazolyl, benzoxazolyl, benzothiazolyl, benzothienyl, quinolinyl, quinazolinyl, naphthyridinyl, indazolyl, triazolyl and purinyl. The structures of the above will be apparent to one skilled in the art, other specific examples include:

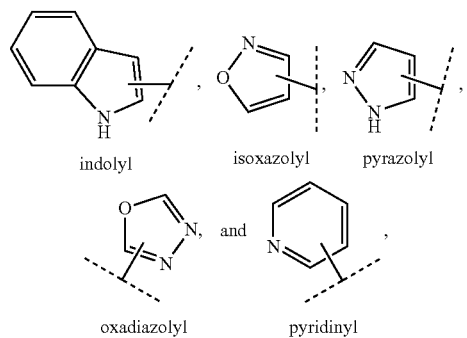

indolyl    isoxazolyl    pyrazolyl oxadiazolyl    pyridinyl and all the possible hydrogenated forms thereof.

Halogen encompasses fluorine, chlorine, bromine and/or iodine atoms.

Each of the above alkyl, cycloalkyl, aryl, heteroalkyl, heterocyclyl or heteroaryl, or any other substituent recited in this application, shall be understood to be optionally fully or partially halogenated where possible, preferably by Cl, F or Br.

Haloalkyl is a fully or partially halogenated alkyl as defined hereinabove, for example trifluoromethane: F$_3$C—.

Any ring structure which has shown this bond

such bond shall be understood to be covalently attached to another moiety at the dashed line and covalently attached at any point in the ring (floating) that will replace a hydrogen atom and result in a stable bond, for example

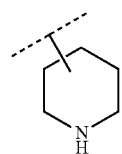

represent piperidinyl attached at the 1, 2, 3 or 4 position.

Features and advantages of the present invention will become apparent from the following detailed Examples, which illustrate the fundamentals of the invention by way of example, without restricting its scope.

General Synthetic Methods

The invention also provides processes for making compounds of Formula (I). In all methods, unless specified otherwise, Ar, R, $R^1$, and, $R^2$ and X in the formulas below shall have the meaning of Ar, R, $R^1$, and, $R^2$ and X in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

General Scheme

Compounds of Formula (I) may be prepared as described in Scheme 1

Scheme 1

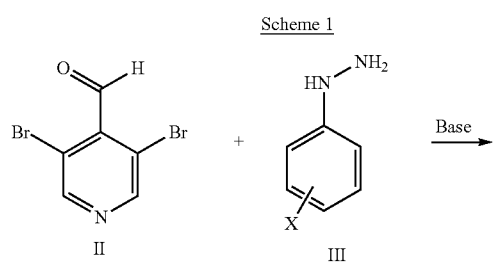

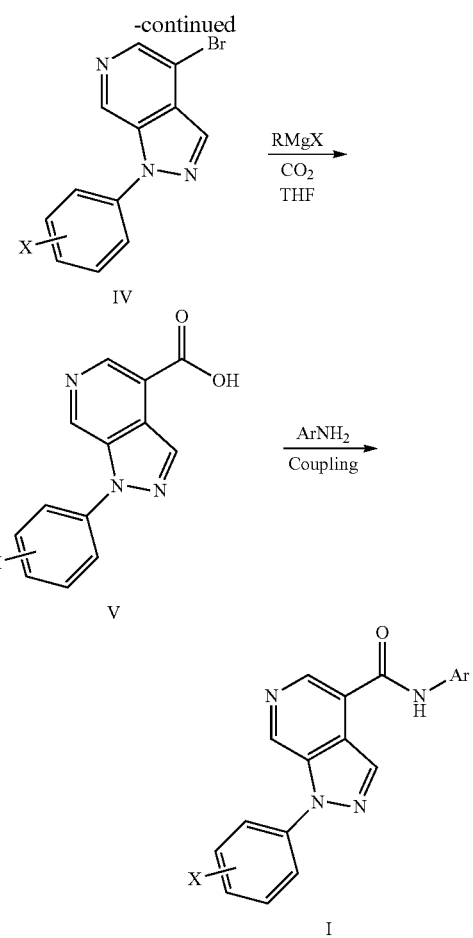

As described above, intermediate II is heated with the substituted phenyl hydrazine III in a suitable solvent such as 1-methyl-2-pyrrolidinone (NMP) in the presence of a suitable base such as 50% aqueous KOH to provide intermediate IV. Intermediate IV is then reacted with a suitable Grignard reagent RMgBr, where R is an alkyl group, such as isopropylmagnesium bromide, followed by addition of $CO_2$ to provide the carboxylic acid intermediate V. This is then coupled with the desired $ArNH_2$ under standard coupling conditions known in the art, for example, by treatment with 2-(1H-7-azabenzotriazol-1-yl)-1,1,3,3-tetramethyl uronium hexafluorophosphate (HATU) in the presence of a suitable base such as N,N-diisopropylethylamine (DIEA) in a suitable to solvent such as dimethylacetamide or by treatment of intermediate V with oxalyl chloride and DMF in a suitable solvent such as dichloromethane (DCM), followed by treatment with the desired $ArNH_2$ to provide the desired compound of Formula (I).

SYNTHETIC EXAMPLES

General Methods

All reactions were run at room temperature unless otherwise noted. All compounds were characterized by LCMS. Retention times are reported in Table I and obtained using a Waters Aquity UPLC with 1 uL injections onto an Acquity UPLC BEH C18 2.1×50 mm column with a 1.7 um particle diameter at 60° C. and the following mobile phases with the indicated gradient:

| Mobile phase A: 95% water 5% acetonitrile 0.05% formic acid |||
|---|---|---|
| Mobile phase B: acetonitrile 0.05% formic acid |||
| Time (min.) | % A | % B |
| 0.00 | 90 | 10 |
| 1.19 | 5 | 95 |
| 1.70 | 5 | 95 |
| 1.72 | 90 | 10 |

Example 1

Preparation of 1-(4-fluoro-phenyl)-1H-pyrazolo[3,4-c]pyridine-4-carboxylic acid (5-methanesulfonyl-2,4-dimethyl-phenyl)-amide (compound 3, Table 1)

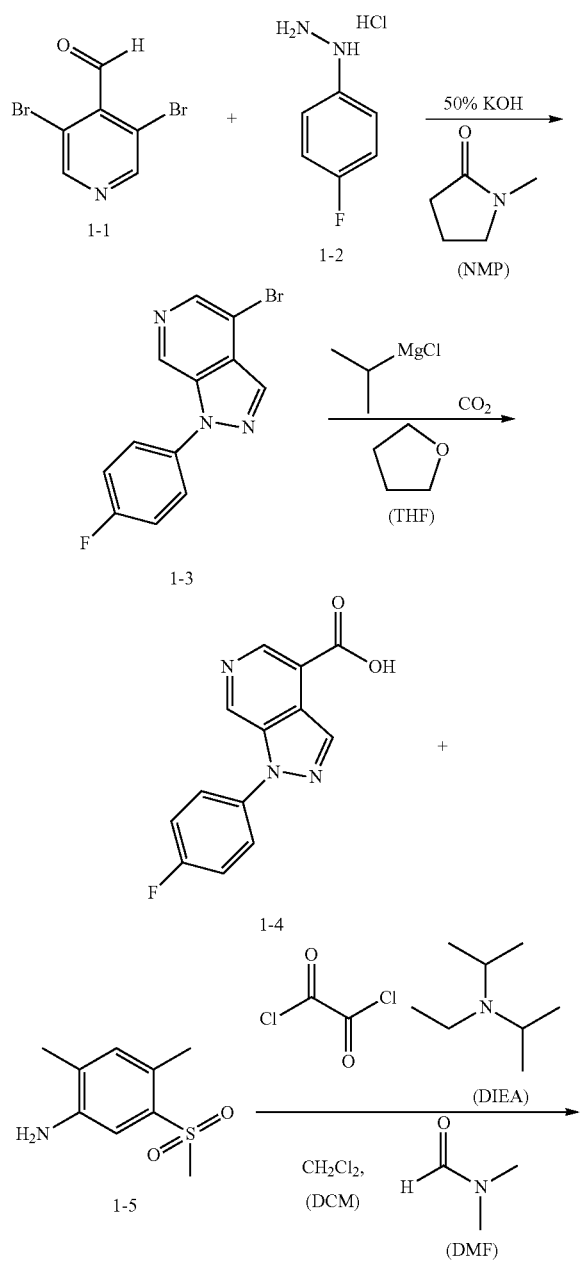

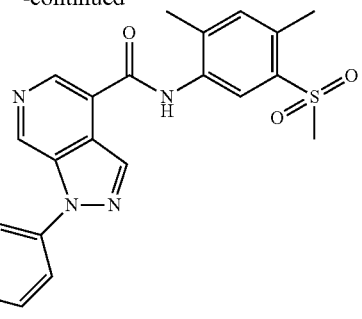

Compound 1-1 (50.0 g, 188.7 mmol) and compound 1-2 (31.0 g, 190.7 mmol) are combined in a flask and treated with NMP (250 mL) and the resulting mixture is stirred for 2 hours. 50% aqueous KOH solution (27.4 g, 415.2 mmol KOH in 27.4 mL water) is then added and the resulting mixture is heated at 80° C. for 60 minutes. Water is then added at 80° C. and the resulting mixture is cooled to ambient temperature over 4-16 hours. The resulting solid is collected by filtration, washed with water and dried to afford compound 1-3 as a solid (51.5 g).

Compound 1-3 (50.0 g, 171.1 mmol) is treated with THF (300 mL) and the resulting mixture is cooled to −20° C. Iso-propylmagnesium chloride solution (128.2 mL, 256.4 mmol, 2.0M in THF) is then added at a rate which maintains the temperature below −10° C. The reaction is stirred at −10° C. for 3 hours at which point $CO_2$ gas is bubbled through the reaction until no temperature increase is observed. The mixture is warmed to ambient temperature and isopropanol (325 mL) is added followed by aqueous HCl (10 mL, 2.6M). The reaction is then heated to 55° C., aqueous HCl (240 mL, 2.6M) is added, and the mixture is cooled to ambient temperature. The resulting solids are collected by filtration and washed with water and isopropanol to give compound 1-4 as a solid (38.4 g).

Compound 1-4 (50 mg, 0.194 mmol) is treated with DCM (2 mL) and oxalyl chloride (33.8 μL, 0.39 mmol) is added dropwise. The resulting mixture is stirred for 10 minutes at which time a drop of DMF is added. The resulting mixture is stirred for 90 minutes after which time the solvent is removed in vacuo. The residue is treated with DCM (1 mL) and the solvent is again removed in vacuo. The resulting residue is treated with DCM (1 mL) and the resulting mixture is added to a mixture of compound 1-5 (77.3 mg, 0.39 mmol) and DIEA (68 μL, 0.39 mmol) and DCM (1 mL). The resulting mixture is shaken for 15 hours after which time methanol (0.5 mL) is added and the mixture is concentrated and purified directly on a reversed phase C18 semi-preparative HPLC column (using a solvent gradient from 10% $H_2O$ in acetonitrile to 100% acetonitrile with 0.1% formic acid as buffer) to provide the title compound (15.4 mg) as a solid. The following compounds are synthesized in similar fashion from the appropriate intermediates:

Compounds 1-2, table 1

Compounds 4-18, table 1

Example 2

Preparation of 1-(4-fluoro-phenyl)-1H-pyrazolo[3,4-c]pyridine-4-carboxylic acid (2,4-dimethyl-pyridin-3-yl)-amide (compound 21, table 1)

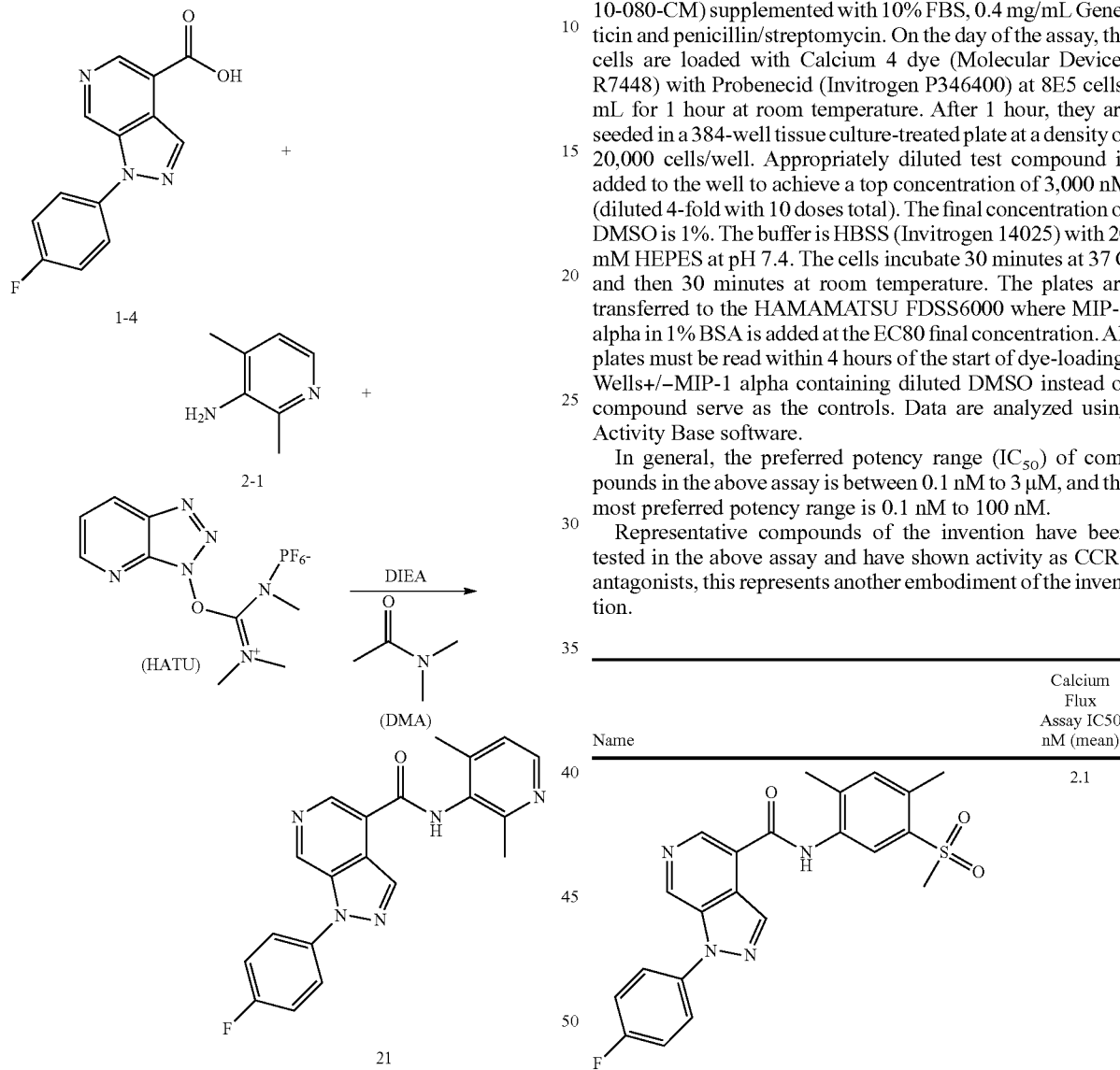

Compound 2-1 (14.4 mg, 0.12 mmol) is treated with compound 1-4 (Example 1) (25.0 mg, 0.098 mmol), DMA (1.8 mL), DIEA (0.05 mL, 0.39 mmol), and HATU (50.0 mg, 0.132 mmol). The resulting mixture is shaken for 16 hours and purified directly on a reversed phase C18 semi-preparative HPLC column (using a solvent gradient from 10% $H_2O$ in acetonitrile to 100% acetonitrile with 0.1% formic acid as buffer) to provide the title compound (6.3 mg) as a solid.

The following compounds are synthesized in similar fashion from the appropriate intermediates:

Compounds 19-20, table 1

Compounds 22-26, table 1

Assessment of Biological Properties

Compounds are assessed for the ability to block the interaction of CCR1 and MIP-1α in a functional cellular assay measuring calcium flux in CCR1 transfected cells.

Non-adherent cells purchased from Chemicon Corporation (HTS005C), stably expressing recombinant CCR1 and G-alpha-16 are grown in RPMI 1640 medium (Mediatech 10-080-CM) supplemented with 10% FBS, 0.4 mg/mL Geneticin and penicillin/streptomycin. On the day of the assay, the cells are loaded with Calcium 4 dye (Molecular Devices R7448) with Probenecid (Invitrogen P346400) at 8E5 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells incubate 30 minutes at 37 C and then 30 minutes at room temperature. The plates are transferred to the HAMAMATSU FDSS6000 where MIP-1 alpha in 1% BSA is added at the EC80 final concentration. All plates must be read within 4 hours of the start of dye-loading. Wells+/−MIP-1 alpha containing diluted DMSO instead of compound serve as the controls. Data are analyzed using Activity Base software.

In general, the preferred potency range ($IC_{50}$) of compounds in the above assay is between 0.1 nM to 3 μM, and the most preferred potency range is 0.1 nM to 100 nM.

Representative compounds of the invention have been tested in the above assay and have shown activity as CCR1 antagonists, this represents another embodiment of the invention.

| Name | Calcium Flux Assay IC50 nM (mean) |
|---|---|
| (structure) | 2.1 |
| (structure) | 2.8 |

| Name | Calcium Flux Assay IC50 nM (mean) |
|---|---|
| 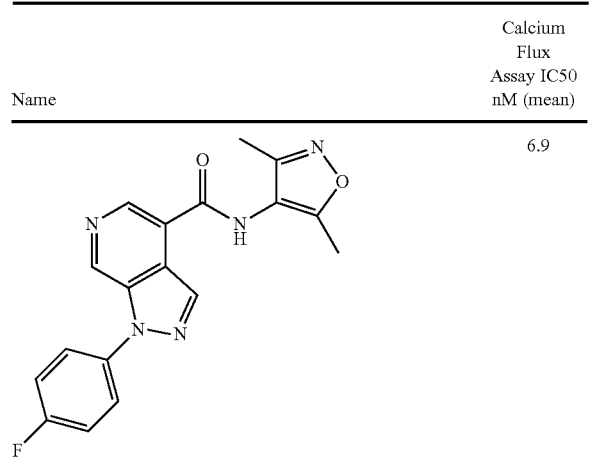 | 6.9 |
| | 8.8 |
| | 14 |
| | 19 |
| Name | Calcium Flux Assay IC50 nM (mean) |
|---|---|
| 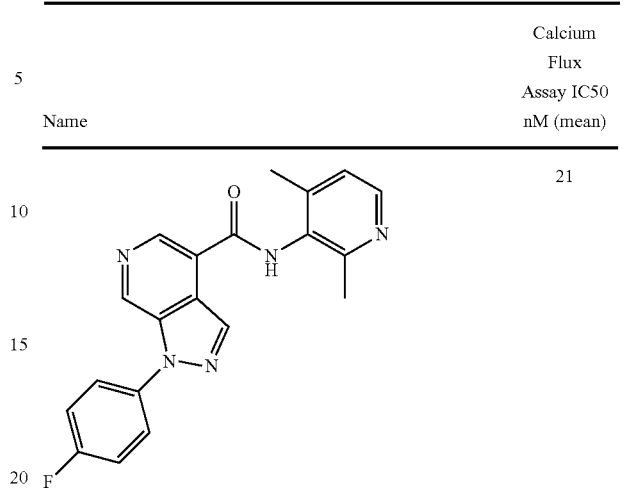 | 21 |
| | 24 |
| | 30 |
| 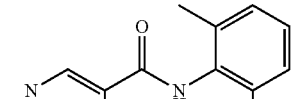 | 36 |

| Name | Calcium Flux Assay IC50 nM (mean) |
|---|---|
| 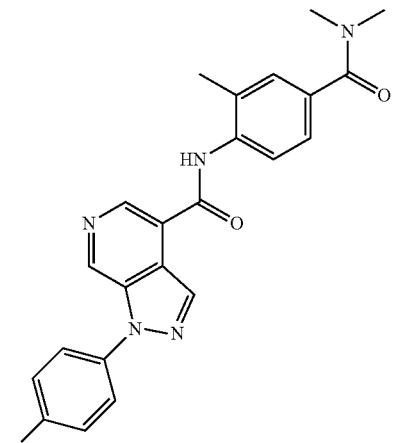 | 66 |
| 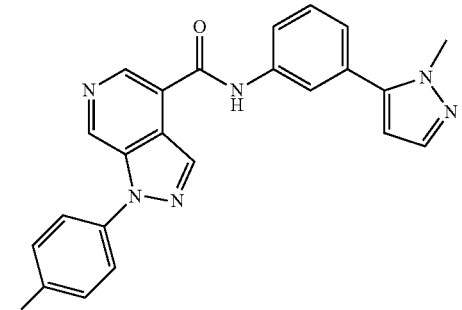 | 73 |
| 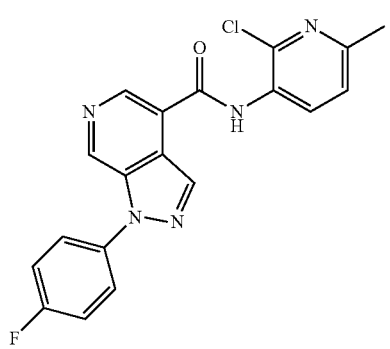 [SMILES: Cc1ccc(NC(=O)c2cncc3c2cnn3-c2ccc(F)cc2)c(Cl)n1] | 82 |
| 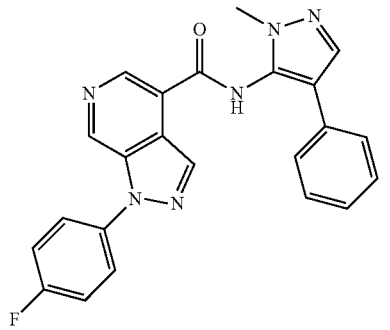 | 84 |

| Name | Calcium Flux Assay IC50 nM (mean) |
|---|---|
| 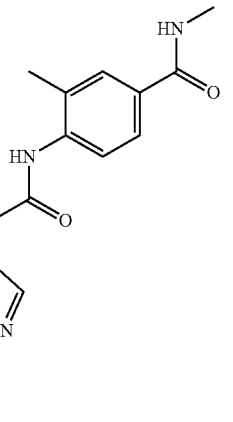 | 93 |

Method of Treatment

The compounds of the invention are effective antagonists of the interactions between CCR1 and its chemokine ligands and thus inhibit CCR1-mediated activity. Therefore, in one embodiment of the invention, there is provided methods of treating autoimmune disorders using compounds of the invention. In another embodiment, there is provided methods of treating inflammatory disorders using compounds of the invention.

Without wishing to be bound by theory, by antagonizing the interactions between CCR1 and its chemokine ligands, the compounds block chemotaxis of pro-inflammatory cells including monocytes, macrophages dendritic cells, eosinophils, and T cells (TH1) cells and other CCR1 positive cells to inflamed tissues and thereby ameliorate the chronic inflammation associated with autoimmune diseases. Thus, the inhibition of CCR1 activity is an attractive means for preventing and treating a variety of autoimmune disorders, including inflammatory diseases, autoimmune diseases, organ (Horuk et al. (2001) *JBC* 276 p. 4199) and bone marrow transplant rejection and other disorders associated with an influx of pro-inflammatory cells. For example, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection), Alzheimer's disease (Halks-Miller et al. (2003) *Ann Neurol* 54 p. 638), Asthma (Jouber et al. (2008) *J. Immun* 180 p. 1268), chronic kidney disease (Topham et al. (1999) *J. Clin. Invest.* 104 p. 1549), sepsis (He et al. (2007) *Am J. Physio* 292 p. G1173), autoimmune myocarditis (Futamats et al. (2006) *J Mol Cell Cardiology* 40 p. 853), multiple myeloma (*Blood* (2001) 97 pp 3349-3353), COPD (*Expert Opin. Investig. Drugs* (2005) 14 pp 785-796) and systemic lupus erythematosus. In particular, the compounds may be used to prevent or treat rheumatoid arthritis and multiple sclerosis. Other disorders associated with the trafficking of pro-inflammatory cells will be evident to those of ordinary skill in the art and can also be treated with the compounds and compositions of this invention.

In a further aspect of the present invention the present invention relates to methods for the treatment of above mentioned diseases and conditions, which method comprises the administration of an effective amount of a compound of the formula (I) to a human being.

Dosage levels and requirements are well-recognized in the art and may be selected by those of ordinary skill in the art from available methods and techniques suitable for a particular patient. In some embodiments, dosage levels range from about 10-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The compounds of the formula (I) may be used on their own or in combination with other active substances according to the invention, optionally also in combination with other pharmaceutically active substances.

Pharmaceutical Compositions:

The instant invention provides a bulk composition comprised of a CCR1 inhibitor of the formula (I) having desirable stability and purity wherein the purity is greater than 90%, 95% or 99%. The composition may additionally comprise in varying percentage, salts, solvates, hydrates, polymorphic forms, and the like, is intended to equally apply to the salt, solvate, hydrates, polymorphic forms of enantiomers, diastereomers, tautomers, racemates of the compounds of the formula (I).

The bulk composition comprised of a CCR1 inhibitor of the formula (I) may be a pharmaceutical composition comprising as an effective amount of the active ingredient which is at least one compound of formula (I). The pharmaceutical composition of formula (I) additionally comprising at least one pharmaceutically acceptable carrier and/or adjuvant. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. Methods for preparing such dosage forms are known. The content of the pharmaceutically active compound(s) should be in the range from contain at least about 15%, but more preferably at least about 20%, of a compound of the invention (w/w) or a combination thereof.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

The invention claimed is:

1. A compound of the formula (I):

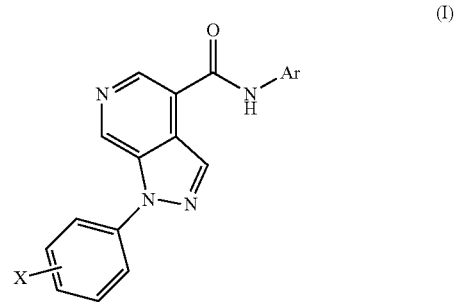

wherein

Ar is phenyl, naphthyl or heteroaryl chosen from aziridinyl, thienyl, furanyl, thiazolyl, isothiazolyl, isoxazolyl, oxazolyl, oxadiazolyl, pyrazolyl, thiadiazolyl, tetrazolyl, pyrrolyl, imidazolyl, pyrimidinyl, pyridinyl, pyrazinyl, pyridazinyl, pyranyl, benzofuranyl, indolyl, quinoxalinyl, benzimidazolyl, benzoxazolyl, benzothiazolyl, benzothienyl, quinolinyl, quinazolinyl, naphthyridinyl, indazolyl, triazolyl and purinyl each bearing from 0-4 substituents chosen from halogen, $C_{1-5}$ alkyl, $C_{3-7}$ cycloalkyl, $C_{1-5}$ haloalkyl, cyano, nitro, —SR, —OR, —SO$_2$R, —SO$_2$NRR$^1$, —NR$^1$—SO$_2$R, —CO$_2$—R, —NRR$^1$, —NR$^2$C(O)—R, —C(O)NRR$^1$, aryl ring and 5- or 6-membered heteroaryl ring each ring optionally substituted with 1 or 2 substituents chosen from halogen and $C_{1-5}$ alkyl;

R, R$^1$, and, R$^2$ are each independently hydrogen or $C_{1-5}$ alkyl;

X is halogen;

or a pharmaceutically acceptable salt thereof.

2. The compound according to claim 1 and wherein

Ar is phenyl, naphthyl, or heteroaryl chosen from aziridinyl, thienyl, furanyl, thiazolyl, isothiazolyl, isoxazolyl, oxazolyl, oxadiazolyl, pyrazolyl, thiadiazolyl, tetrazolyl, pyrrolyl, imidazolyl, pyrimidinyl, pyridinyl, pyrazinyl, pyridazinyl, pyranyl, benzofuranyl, indolyl, quinoxalinyl, benzimidazolyl, benzoxazolyl, benzothiazolyl, benzothienyl, quinolinyl, quinazolinyl, naphthyridinyl, indazolyl, triazolyl and purinyl each bearing from 0-3 substituents chosen from halogen, $C_{1-4}$ alkyl, $C_{3-7}$ cycloalkyl, $C_{1-4}$ haloalkyl, nitro, —SR, —OR, cyano, —SO$_2$R, —SO$_2$NRR$^1$, —CO$_2$—R, —NRR$^1$, —NR$^2$C(O)—R, —C(O)NRR$^1$, phenyl and heteroaryl as defined herein above in this paragraph, each ring optionally substituted with 1 or 2 substituents chosen from halogen and $C_{1-4}$ alkyl;

R, R$^1$, and, R$^2$ are each independently hydrogen or $C_{1-4}$ alkyl;

X is fluorine;

or a pharmaceutically acceptable salt thereof.

3. The compound according to claim 2 and wherein

Ar is phenyl, pyrazolyl, isoxazolyl, pyridinyl, indolyl, each bearing from 0-3 substituents chosen from halogen, $C_{1-4}$ alkyl, $C_{3-7}$ cycloalkyl, $C_{1-4}$ haloalkyl, nitro, —SR, —OR, cyano, —SO$_2$R, —SO$_2$NRR$^1$, —CO$_2$—R, —NRR$^1$, —NR$^2$C(O)—R, —C(O)NRR$^1$, phenyl and pyrazolyl, oxadiazolyl, each ring optionally substituted with 1 or 2 substituents chosen from halogen and $C_{1-4}$ alkyl;

X is fluorine and is attached in the -para position on the phenyl ring
or a pharmaceutically acceptable salt thereof.

4. The compound according to claim 3 and wherein
Ar is phenyl, pyrazolyl, isoxazolyl, pyridinyl, indolyl, each bearing from 0-3 substituents chosen from halogen, $C_{1-2}$ alkyl, —$CF_3$, —$SO_2CH_3$, —$SO_2NRR^1$, —$CO_2$—R, —$NR^2C(O)$—R, —$C(O)NRR^1$, phenyl and pyrazolyl, oxadiazolyl, each ring optionally substituted with 1 or 2 substituents chosen from halogen and $C_{1-2}$ alkyl;

R, $R^1$, and, $R^2$ are each independently hydrogen or $C_{1-2}$ alkyl;

or a pharmaceutically acceptable salt thereof.

5. The compound according to claim 4 and wherein
Ar is chosen from

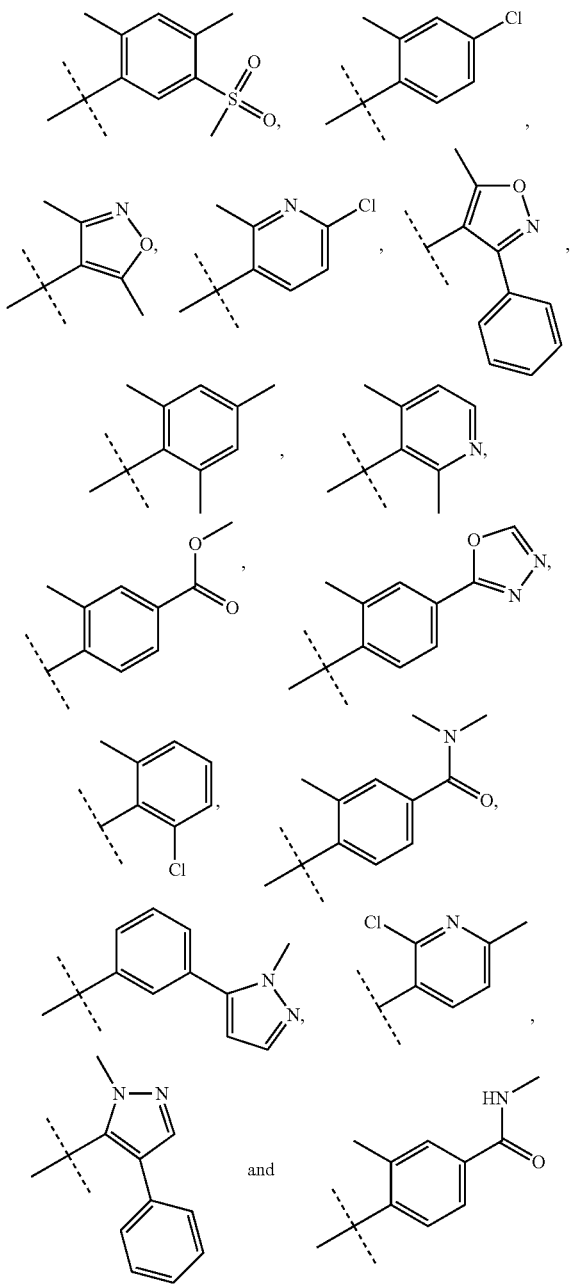

and or a pharmaceutically acceptable salt thereof.

6. A compound chosen from

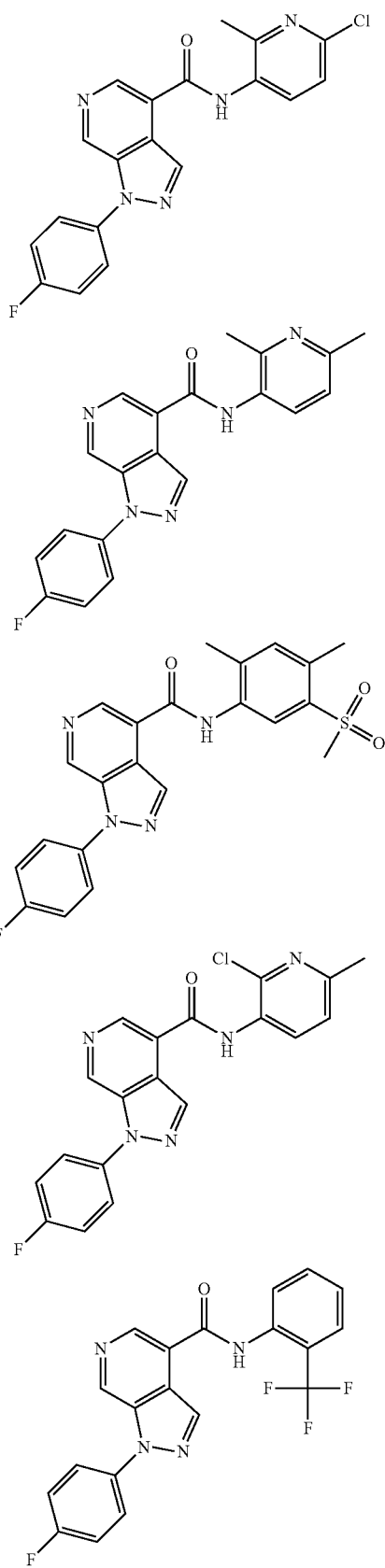

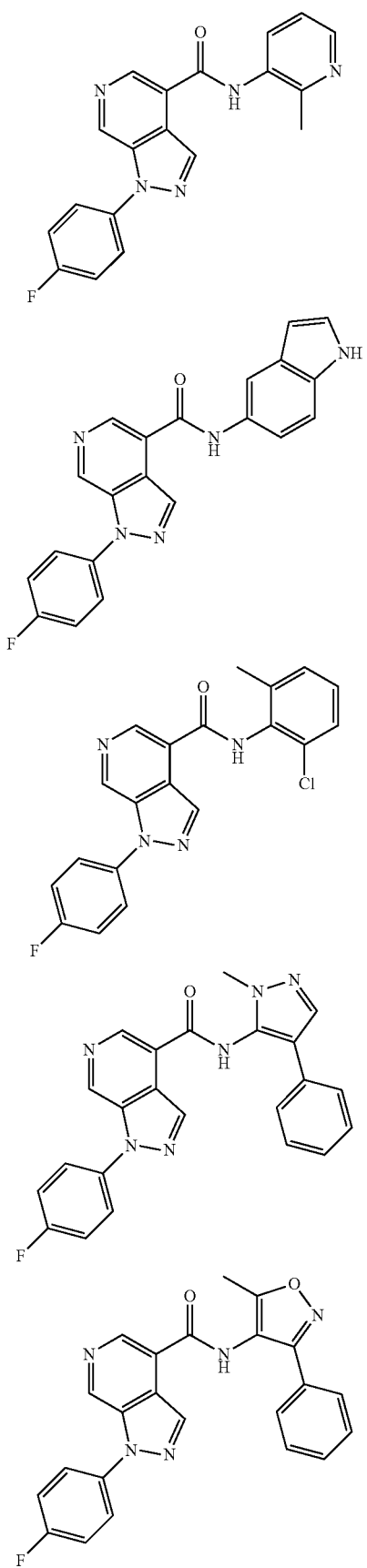 [SMILES: Cc1ncccc1NC(=O)c1cncc2c1cnn2-c1ccc(F)cc1 ; O=C(Nc1ccc2[nH]ccc2c1)c1cncc2c1cnn2-c1ccc(F)cc1 ; Cc1cccc(Cl)c1NC(=O)c1cncc2c1cnn2-c1ccc(F)cc1 ; Cn1ncc(-c2ccccc2)c1NC(=O)c1cncc2c1cnn2-c1ccc(F)cc1 ; Cc1onc(-c2ccccc2)c1NC(=O)c1cncc2c1cnn2-c1ccc(F)cc1]
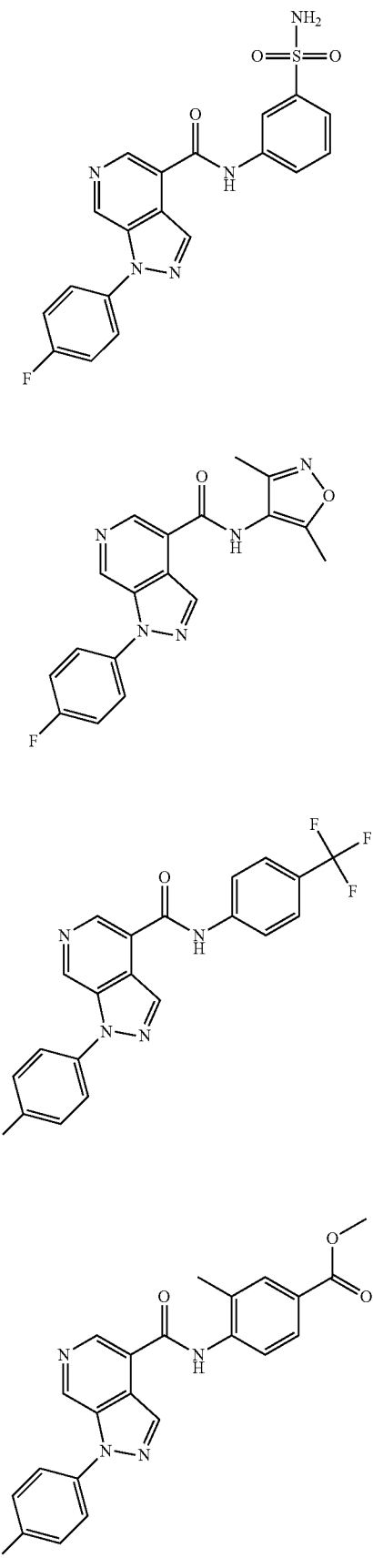

37
-continued
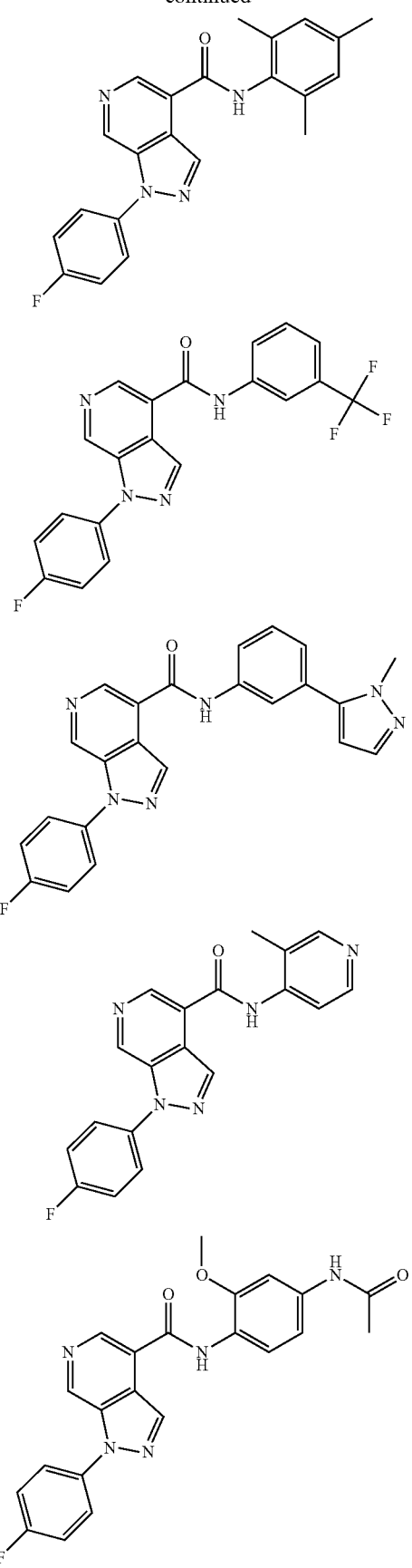
38
-continued
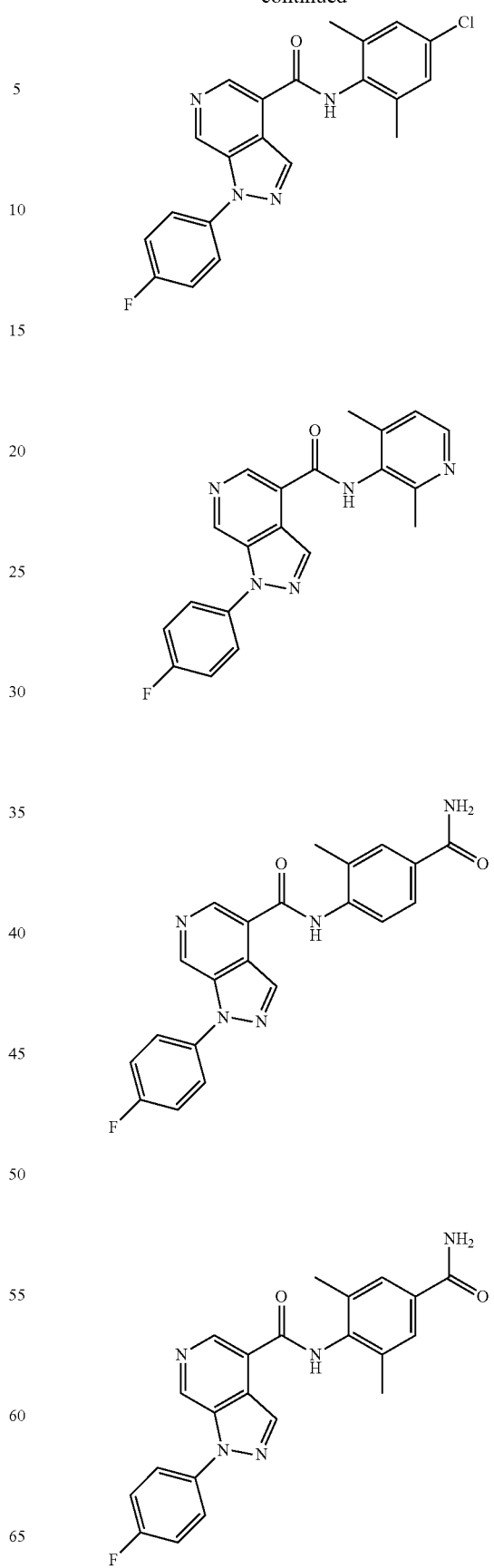

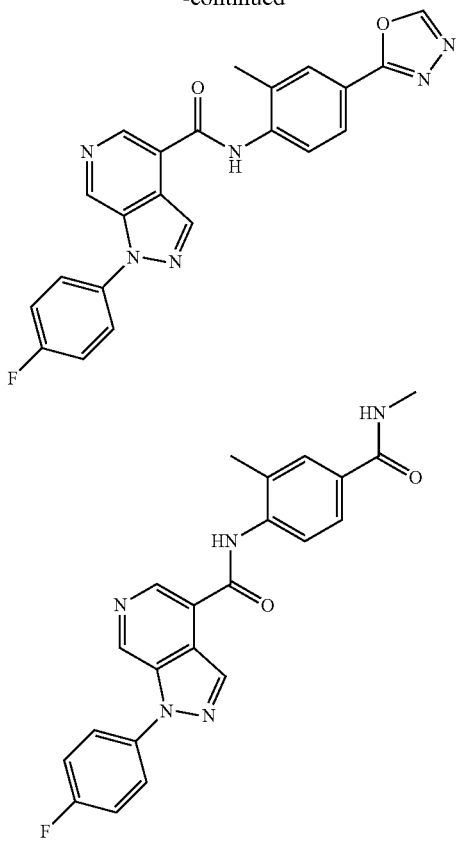

or a pharmaceutically acceptable salt thereof.

7. A pharmaceutical composition comprising a pharmaceutically effective amount of a compound according to claim 1 and one or more pharmaceutically carriers and/or adjuvants.

8. A method of treating rheumatoid arthritis or multiple sclerosis comprising administering to a patient a pharmaceutically effective amount of a compound according to claim 1.

9. The method according to claim 8 wherein the treatment is for rheumatoid arthritis.

10. The method according to claim 8 wherein the treatment is for multiple sclerosis.

* * * * *